United States Patent [19]

Pensack

[11] 4,152,447
[45] May 1, 1979

[54] NOVEL METHOD FOR THE ENHANCEMENT OF WOOL GROWTH

[75] Inventor: Joseph M. Pensack, Trenton, N.J.

[73] Assignee: American Cyanamid Company, Stamford, Conn.

[21] Appl. No.: 910,167

[22] Filed: May 26, 1978

[51] Int. Cl.² .............................................. A61K 31/38
[52] U.S. Cl. .................................................... 424/275
[58] Field of Search ......................................... 424/275

[56] References Cited

U.S. PATENT DOCUMENTS 4,036,979  7/1977  Asato .................................... 424/275

*Primary Examiner*—Frederick E. Waddell
*Attorney, Agent, or Firm*—Harry H. Kline

[57] ABSTRACT

There is provided a method for enhancing wool growth and favorably altering the ratio of secondary to primary wool follicles in fur-bearing animals, such as llamas, sheep, goats, rabbits and chinchillas, by administering at from birth to 15 weeks of age to each of said animals orally or as a subcutaneous implant a 4,5,6,7-tetrahydrobenzo[b]thien-4-ylurea compound in an amount effective to achieve marked wool growth enhancement.

2 Claims, No Drawings

NOVEL METHOD FOR THE ENHANCEMENT OF WOOL GROWTH

The present invention relates to a method for enhancing wool growth and favorably altering the ratio of secondary to primary wool follicles in fur-bearing animals. More particularly, it relates to a method for enhancing wool growth by either administering to a fur-bearing animal orally or implanting subcutaneously a 4,5,6,7-tetrahydro-benzo[b]-thien-4-ylurea compound in an amount effective to achieve wool growth enhancement. Still more particularly, the invention is concerned with the utilization of certain tetrahydro-benzo[b]thien-4-ylurea compounds which possess in vivo biological activity in promoting wool growth and favorably altering the ratio of secondary to primary wool follicles.

In a German application, Offenlegungschrift No. 2501788 published on January 25, 1974, there are disclosed 4,5,6,7-tetrahydro-benzo[b]thien-4-ylurea compounds which can be represented by the formula:

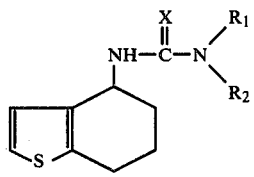

wherein X is oxygen or sulfur; $R_1$ and $R_2$ represent a plurality of substituents to enhance the biological activity of said formula (I) compounds. This application also discloses methods for utilizing said compounds for the control of undesirable plant species, for promoting animal growth and for enhancing feed efficiency. However, the aforementioned application does not teach or suggest that certain tetrahydro-benzo[b]thien-4-ylurea compounds of the present invention are effective for the enhancement of wool growth, and for favorably altering the ratio of secondary to primary wool follicles in fur-bearing animals, such as llamas, sheep, goats, rabbits, chinchillas, and the like.

It is known that the wool follicle in the sheep is an epidermal structure which produces wool fibers. Follicle development begins in the lamb at about 50 days of fetal age. The follicles formed first, which tend to be larger, and are termed primary follicles, acquire sweat glands and erector muscles. The quota of primary follicles is fully established before birth. Follicles beginning to form at about 90 days of fetal life, the secondary follicles, tend to be smaller than the primaries and develop only sebaceous glands. Proliferation of secondary follicles continue for a short time after birth. This critical period, during which the number of secondary follicles unalterably and fully establish themselves, varies from breed to breed. In Suffolk sheep, for instance, this period ends at about 6 weeks after birth, whereas, for Merino sheep, this period can be as long as 12 to 15 weeks.

In general, three main kinds of fiber are recognized in adult sheep. These are wool fibers, hair fibers and kemps, although they are collectively loosely regarded as wool. Wool fibers are fine (15–40 microns in diameter), tightly crimped and lack a medulla. Kemp fibers are very coarse (about 100 microns in diameter) and are fairly short in length. Kemp is undesirable in good wool because it takes up dye poorly and it also causes brittleness. Hairs are intermediate between wool and kemp fibers. They range in diameter from 50 to 100 microns. Kemp fibers grow only in primary follicles; whereas, hair and wool can grow in both primary and secondary follicles depending on the breed.

At birth, the follicles are packed closely together in the skin and so the follicle density is high. The number of follicles per square centimeter usually range between 3,000 and 4,000 in a Down breed; whereas, in the Australian Merino the follicle density at birth may be more than 10,000. As the animal grows, the skin expands and the follicle density decreases, so that adult figures are about 1,000 follicles per square centimeter in a mountain breed such as the Scottish Blackface, about 1,500 in longwools, 2,000 to 3,000 in Down breeds and between 5,000 and 10,000 in different strains of the Merino. In general, the greater the follicle density, the finer is the fleece.

The numbers of secondaries to primaries (S/P ratio) are the best indication of the condition of follicle population in relation to wool productivity. Since the secondary follicles are wool producing, it follows that the ratio of S/P determines the wool productive capacity of sheep. The S/P ratio in the Suffolk sheep is 5:1; whereas, it is about 22:1 in the Merino whose wool producing capacity is very high. If the number of secondaries could be increased in a sheep, that sheep would therefore produce more wool, thereby enhancing the state of the art.

Surprisingly, it has been found that wool growth enhancement is attained by the method of the present invention which comprises administering to a fur-bearing animal at from birth to not more than 15 weeks after birth a compound of the formula:

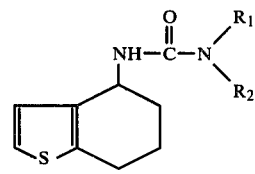

wherein $R_1$ is a hydrogen, $C_1$–$C_3$ alkyl, allyl, 2-propynyl or methoxy; $R_2$ is hydrogen or $C_1$–$C_3$ alkyl. The compound when implanted subcutaneously or administered orally, unexpectedly, is found to enhance wool growth and favorably alter the ratio of secondary to primary wool follicles in said animals.

For purposes of the aforementioned utility, the most preferred compound of the formula illustrated and defined above, is 4,5,6,7-tetrahydro-benzo[b]thien-4-ylurea, although 1-methyl- or 1-methoxy-3-(4,5,6,7-tetrahydro-benzo-[b]thien-4 yl)urea may be employed.

In practice, a wool growth-promoting and/or a follicle ratio altering amount of a tetrahydro-benzo[b]-thien-4-ylurea compound is administered to a host animal usually with the animal's feed. However, said compound may also be implanted as one or more subcutaneous implants under the skin of said animal. When administered in the feed of llamas, sheep, goats, rabbits, chinchillas, and the like, usually about 10 ppm to 70 ppm, and preferably from 15 ppm to 60 ppm, by weight of the compound, is effective for increasing wool growth and favorably altering the secondary to primary wool follicle ratio. When administered as a subcutaneous implant, usually in amounts that supply about 0.0005 mg to 0.2 mg, and preferably 0.001 mg to 0.10 mg per kg of body weight per day of active compound, produce the desired improvement in wool growth and/or secondary to primary wool follicle ratio.

The invention may be better understood by referring to the examples provided below which are to be taken as merely illustrative. Unless otherwise specified, the parts are given by weight and the analysis is in percent.

EXAMPLE 1

Evaluation of the Effect of 4,5,6,7-Tetrahydro-benzo[b]-thien-4-ylurea Implants on Favorably altering the Secondary to Primary Wool Follicle Ratio in Sheep Ten sets of twin lambs are implanted at birth. One lamb of each pair receives three implants (36 mg of compound) in the ear subcutaneously, and the other lamb of the pair receives three implants of castorwax. Skin samples are taken at birth and at 6 weeks of age. The data obtained are averaged and summarized in Table 1 below.

TABLE I

Evaluation of the Effect of 4,5,6,7-Tetrahydro-benzo[b]thien-4-ylurea Implants on Favorably Altering the Secondary to Primary Wool Follicle Ratio

| Group | Ratio of Secondary/Primary Wool Follicle At Birth | Ratio of Secondary/Primary Wool Follicle At 6 Weeks of Age | Change in Ratio at 6 Weeks | Percent Change in Ratio at 6 Weeks Over Controls |
|---|---|---|---|---|
| Control | 2.84 | 5.69 | 2.86 | |
| Treated | 3.06 | 6.69 | 3.56 | 24.47 |

It can be seen from Table I that the compound of the invention favorably alters the ratio of secondary to primary wool follicles.

EXAMPLE 2

Evaluation of the Effect of 4,5,6,7-Tetrahydro-benzo[b]-thien-4-ylurea on the Enhancement of Wool Growth and Wool Staple Length The lambs utilized in Example 1 are grazed on a high alpine pasture. Six months from the date of implantation, the lambs are shorn. Greasy fleece weight, staple length and fiber diameter are determined. The data obtained are averaged and summarized in Table II below.

TABLE II

Evaluation of the effect of 4,5,6,7-Tetrahydrobenzo[b]thien-4-ylurea on Enhancing Wool Growth, Staple Length and Fiber Diameter

| Group | Greasy Fleece Weight in kg | Greasy Fleece Percent | Staple Length in cm | Staple Percent | Fiber Diameter in Microns |
|---|---|---|---|---|---|
| Control | 1.783 | 100 | 7.45 | 100 | 23.72 |
| Treated | 1.9096 | 107.12 | 8.45 | 113.42 | 23.95 |

It can be seen from Table II that the compound of the invention enhances wool growth and staple length.

EXAMPLE 3

Weaned young lambs are randomly allotted to pens in groups of thirty. The animals are offered water and feed ad libitum. These lambs receive the same diet as control animals, but with the addition of 4,5,6,7-tetrahydrobenzo[b]thien-4-ylurea at a concentration of 15 ppm. The composition of the lamb diet employed in this example is set forth in Table III below.

TABLE III

| Component | Percent By Weight |
|---|---|
| Ground Corn Cob | 15.0 |
| Ground Yellow Corn | 48.0 |
| Soybean Oil Meal (49%) | 10.0 |
| Dehydrated Alfalfa Meal | 15.0 |
| Molasses | 10.0 |
| Iodized Salt | .5 |
| Dicalcium Phosphate | 1.0 |
| Premix | 0.5 |
| | 100.0 |
| Premix for One Ton | |
| Tra-Min No. 3[(1)] | 454 grams |
| Vitamin A (30,000 μ/g) | 133 grams |
| Vitamin D$_3$ (200,000 μ/g) | 5 grams |
| Corn Oil | 100 grams |
| Ground Corn | 3848 grams |
| | 4540 grams |
| [(1)]Tra-Min No. 3 comprises: | |
| Calcium | 21.00% |
| Manganese | 12.50% |
| Iron | 6.00% |
| Zinc | 5.00% |
| Copper | 0.65% |
| Iodine | 0.35% |
| Cobalt | 0.25% |

Two days before the start of the feeding, an area 15 cm wide by 25 cm long, starting directly behind the right shoulder, and approximately 10 cm from the midline, of each lamb is shorn with an Oster hair clipper equipped with a fine No. 40 cutting blade. After feeding for 56 days, a wool sample is taken from the same area by close clipping, a section 4.5 cm wide and 15 cm long. This wool sample is weighed (grease weight) and then scoured to remove oil and particulate matter.

Resultant scoured wool is placed in tared aluminum weigh pans and dried for 12 hours. The dried wool is allowed to cool in a desiccator before weighing.

Wool fiber length is determined by measuring four separate bundles of fiber with a vernier caliper under a dissecting lamb exhibiting the marked improvement of Example 2. The results of the feeding study are similar to those obtained in Example 1.

I claim:

1. A method for increasing fiber length and increasing secondary to primary wool follicle ratio in sheep comprising: parenterally administering to said sheep at birth a compound of the formula:

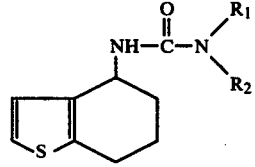

wherein R$_1$ is a member selected from the group consisting of hydrogen, C$_1$-C$_3$ alkyl, allyl, 2-propynyl and methoxy; R$_2$ is hydrogen or C$_1$-C$_3$ alkyl, whereby secondary to primary wool follicle ratio and wool fiber length are markedly increased, said compound being sufficient to provide a daily drug release of from 0.0005 mg to 0.2 mg of said compound per kg of animal body weight.

2. The method according to claim 1, wherein said compound is 4,5,6,7-tetrahydrobenzo[b]thien-4-ylurea.

* * * * *